（12）United States Patent
Davidson et al.

(10) Patent No.: US 7,034,302 B2
(45) Date of Patent: Apr. 25, 2006

(54) OPTICAL STEAM QUALITY MEASUREMENT SYSTEM AND METHOD

(75) Inventors: James R. Davidson, Idaho Falls, ID (US); Judy K. Partin, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 156 days.

(21) Appl. No.: 10/251,318

(22) Filed: Sep. 19, 2002

(65) Prior Publication Data

US 2004/0056197 A1    Mar. 25, 2004

(51) Int. Cl.
*G01J 5/02*        (2006.01)

(52) U.S. Cl. ............... 250/339.1; 250/339.06

(58) Field of Classification Search ........... 250/339.06, 250/339.01, 338.1, 336.1, 345; 356/335, 356/336
See application file for complete search history.

(56) References Cited

U.S. PATENT DOCUMENTS

| | | | |
|---|---|---|---|
| 4,137,462 A | | 1/1979 | Wyler |
| 4,497,577 A | | 2/1985 | Sato et al. |
| 4,862,001 A | * | 8/1989 | Dowling et al. ............ 250/345 |
| 5,383,024 A | | 1/1995 | Maxey et al. |
| 5,737,104 A | * | 4/1998 | Lee et al. ...................... 398/79 |
| 5,870,192 A | * | 2/1999 | Barker ........................ 356/477 |
| 6,128,079 A | | 10/2000 | McCloskey et al. |
| 6,337,660 B1 | * | 1/2002 | Esman et al. ................ 342/375 |
| 6,633,037 B1 | * | 10/2003 | Toomey .................... 250/341.1 |
| 6,731,855 B1 | * | 5/2004 | Chang et al. ................ 385/140 |

* cited by examiner

*Primary Examiner*—David Porta
*Assistant Examiner*—Christine Sung
(74) *Attorney, Agent, or Firm*—TraskBritt, P.C.

(57) ABSTRACT

An optical measurement system is presented that offers precision on-line monitoring of the quality of steam. Multiple wavelengths of radiant energy are passed through the steam from an emitter to a detector. By comparing the amount of radiant energy absorbed by the flow of steam for each wavelength, a highly accurate measurement of the steam quality can be determined on a continuous basis in real-time. In an embodiment of the present invention, the emitter, comprises three separate radiant energy sources for transmitting specific wavelengths of radiant energy through the steam. In a further embodiment, the wavelengths of radiant energy are combined into a single beam of radiant energy for transmission through the steam using time or wavelength division multiplexing. In yet a further embodiment, the single beam of radiant energy is transmitted using specialized optical elements.

65 Claims, 4 Drawing Sheets

OPTICAL STEAM QUALITY MEASUREMENT SYSTEM AND METHOD

GOVERNMENTAL LICENSE RIGHTS

The United States Government has certain rights in this invention pursuant to Contract No. DE-AC07-99ID13727, and Contract No. DE-AC07-05ID14517 between the United States Department of Energy and Battelle Energy Alliance, LLC.

BACKGROUND OF THE INVENTION

1. Field of the Invention

The present invention relates generally to measuring the quality, or wetness, of steam. More particularly, the present invention relates to an optical system and method for determining the quality of a flow of steam by using laser diode emitter and photo diode detector devices to measure radiant energy absorption due to liquid water in the flow of steam.

2. State of the Art

The efficiency and lifetime of components in steam systems are affected by the quality, or wetness, of the steam. Steam quality is defined as the percentage of the total fluid mass of steam that is in the vapor phase. "Dry" steam or steam of 100% quality consists solely of water in the vapor phase. Steam quality of less than 100% indicates the steam contains a portion of water in the liquid phase corresponding to the reduction in quality percentage. Such steam is referred to as "wet" steam. The portion of water in the liquid phase is often due to condensation caused by temperature drops or other energy losses at points throughout a steam system. Excessive steam washing to remove particulates or reduce concentrations of chloride or other impurities to levels that are non-damaging to system components can also introduce excess moisture. The resulting wet steam carries water droplets that can corrode system components such as turbine blades or piping, eventually resulting in failure thereof. In addition, entrained water droplets often contain solids that can deposit on turbine surfaces, adversely affecting the flow stream and turbine efficiency as well as potentially causing imbalance and necessitating cleaning operations. Wet steam also contains less usable energy than dry steam, translating into a loss in mechanical performance. Control of steam quality during operation can be used to anticipate and correct these problems. Accordingly, online or "real time" monitoring and feedback of steam quality is important for diagnostic purposes to increase operating efficiency and to reduce equipment maintenance and replacement costs.

Historically, calorimeters have been used to measure steam quality, but difficulties with sensitivity, accuracy and range limit their suitability for use in many applications. Moreover, calorimeters in most cases require slip stream installations and the insertion of multi-port probes which may disrupt steam flow and result in measurement errors due to nonrepresentative sampling. Calorimeters also exhibit slow response times, making them unsuitable for continuous, real time monitoring. Such continuous monitoring is important if quality measurement of steam is to be used for diagnostic and failure detection purposes. Other attempts to measure steam quality while avoiding the drawbacks of calorimetry have been developed using optical methods. By observing changes in light or other radiant energy passed through a flow of steam, and comparing the changes with known effects of water droplets on the various wavelengths transmitted, a determination of the percentage of liquid water contained in the steam can be made.

In one optical technique, steam quality is measured by comparing the intensity (I) of light passed though a flow of wet steam containing water droplets in suspension to the intensity ($I_o$) of light passed through a flow of dry steam which contains no water droplets. In the wet steam, the light is scattered by the droplets based on the ratio of droplet diameter and the wavelength of the light, thereby reducing its intensity. Under the Mie scattering theory derived from Maxwell's equations, the ratio of intensities ($I/I_o$) can be used to deduce droplet size and distribution, and thereby the amount of liquid water in a given flow of steam. U.S. Pat. No. 6,128,079 to McClosky et al. and U.S. Pat. No. 4,137,462 to Wyler disclose typical examples of this scattering measurement technique, wherein a probe is inserted into a passageway for transmitting a beam of light across a flow of steam and reflecting it back to a photo detector. The invasive nature of this approach raises concerns with respect to the effect of a probe on the flow of steam, which may reduce the accuracy of the scattering measurements. Moreover, scattering of light outside of the measurement area may be reflected back from other surfaces within the passageway, generating noise which must be compensated for by a signal offset.

Another optical technique that has achieved some success is to measure a drop in radiant energy intensity due to absorption by water droplets, rather than scattering. U.S. Pat. No. 4,862,001 to Dowling et al., the disclosure of which is incorporated herein by reference, discloses a steam quality monitor using this technique. Two windows are included on opposite sides of a steam pipe. A source located outside of the steam pipe passes a beam of IR energy through the windows to a detector located on the opposite side of the steam pipe. The loss of IR energy due to absorption by water droplets in the steam is then determined by comparing the energy of the IR beam passed through the steam to one sent from the source to a detector without passing through steam. Using Beer's law, which relates the amount of energy absorbed to the mass of water droplets in a given volume of steam, the steam quality can be calculated. While well known in the prior art, this technique has not been widely used due to the cost and complexity of the instruments required. Large-scale, high-temperature broadband IR sources are required to provide sufficient transmission as the IR energy rarely has the intensity and beam quality necessary for accurate measurements. Broadband IR sources are not collimated and as a result do not present a consistent beam cross section through the measured volume of steam. Since the IR beam may spread quickly, its intensity cross section during transmission across the measured volume changes as a function of the path length. Accordingly, such systems often lack the sensitivity and stability to perform measurements under operating conditions of interest.

What is needed, therefore, is an optical system for measuring steam quality that is sensitive to slight variations in steam quality during real time monitoring while being of a compact and noninvasive nature.

BRIEF SUMMARY OF THE INVENTION

An optical measurement system and method is presented that offers precision on-line monitoring of steam quality which is more versatile and accurate than the above-described prior art techniques. A closed vessel having a chamber or passageway, such as a steam pipe, is provided with first and second windows aligned across the path of a flow or other volume of steam to be contained therein. In operation, at least one wavelength and, in some embodiments, multiple wavelengths of radiant energy are passed through a volume of steam from an emitter associated with the first window to a detector associated with the opposing second window. If multiple wavelengths are employed, by comparing the amount of each wavelength of radiant energy absorbed by the steam, a highly accurate measurement of the steam quality may be determined on a continuous basis in real-time.

The present invention further improves operation by utilizing optical semiconductor-based emitter and detector technology that is robust, light-weight, portable and operates at ambient (room) temperatures. In one aspect of the present invention, for instance, laser diodes are implemented as the source of radiant energy in the emitter. These devices provide high intensity and energy stability, thereby overcoming the problems encountered in prior art optical systems with respect to device size and beam quality. Likewise, in another aspect of the present invention photo diodes are used in the detector to receive the radiant energy, thus providing a compact and reliable monitoring mechanism.

In an exemplary embodiment of the present invention, the emitter comprises three laser diodes which are each coupled to a fiber-optic cable for transmitting specific wavelengths of radiant energy through the volume of steam. The first laser diode generates a radiant energy signal at a wavelength that is significantly absorbed when transmitted through water in the vapor phase. The second laser diode generates a radiant energy signal at a wavelength that is significantly absorbed when transmitted through water in the liquid phase. The third laser diode generates a radiant energy signal at a wavelength that is minimally influenced by water in either state. The detector comprises a number of photo diodes which respectively receive the radiant energy signals after passing through the volume of steam and measure energy losses due to absorption. By comparing the signal losses at the wavelengths generated with the first and second laser diodes, the relative amounts of absorption due to the presence of liquid water and water vapor may be calculated to determine steam quality. The losses at the energy wavelength generated by the third laser diode may be used as a reference to improve the absorption measurements indicated by energy losses in the first and second wavelength signals by providing an indication of signal noise that may be present due to scattering of the radiant energy.

In a further embodiment of the present invention, the radiant energy signals generated by the three laser diodes are combined for transmission into one fiber-optic cable using multiplexing. In this manner, the signals are transmitted transversely across the volume of steam as a single beam of radiant energy. By doing so, the signals each pass through the same volume of the volume of steam, providing for a more precise correlation between the losses for each wavelength. Under one combination approach, the signals are modulated with known frequency domain multiplexing techniques such that a single photo diode is used to receive the beam of radiant energy and measure energy loss for all three signal wavelengths. Under an alternative approach, the signals are combined using known wavelength division multiplexing techniques wherein the beam of radiant energy is received by three separate photo diodes, each of which measures energy loss for a specific signal wavelength.

In yet a further embodiment of the present invention, specialized optical elements are used to guide the beam of radiant energy across the passageway. The emitter includes a collimator with a graded index lens to produce a large diameter beam of radiant energy to pass through the volume of steam. The enlarged cross-sectional area of the beam of radiant energy thereby encompasses a larger sample of steam, enabling more reliable measurements and reducing signal noise due to scattering effects. The detector includes a receiver with a graded index lens for collecting the enlarged beam of radiant energy and passing it to the photo diodes. Use of an enlarged laser beam may, in many instances, remove the need for a third wavelength of radiant energy due to a reduced significance of scattering effects and, in some instances requiring less sensitivity, may enable steam quality measurement using a single wavelength.

Other and further features and advantages will be apparent from the following detailed description of the present invention taken in conjunction with the accompanying drawings. It should be understood that the following is provided for illustrative and exemplary purposes only, and that numerous combinations and modifications of the various embodiments are possible.

BRIEF DESCRIPTION OF THE SEVERAL VIEWS OF THE DRAWINGS

In the drawings, which illustrate what is currently considered to be the best mode for carrying out the invention.

DETAILED DESCRIPTION OF THE INVENTION

Referring in general to the following description and accompanying drawings, various aspects of the present invention are illustrated to show its structure and method of operation. Common elements of the illustrated embodiments are designated with like numerals. It should be understood the figures presented are not meant to be illustrative of actual views of any particular portion of the actual optical measurement system structure, but are merely idealized representations which are employed to more clearly and fully depict the present invention.

Figure 1:
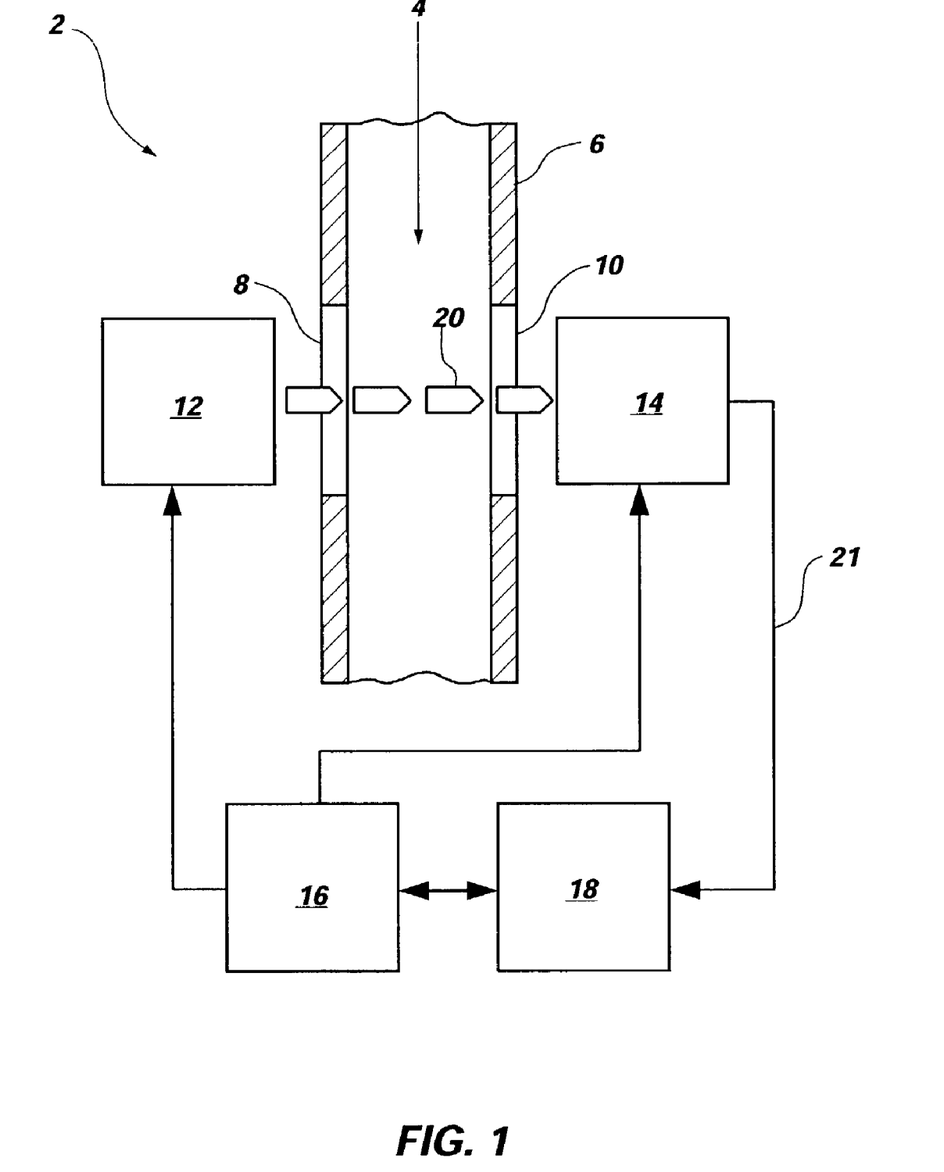
FIG. 1 is a schematic view of an optical measurement system according to the present invention.

FIG. 1 is a schematic view of the optical measurement system 2 according to the present invention being situated to measure the quality of a flow of steam 4 moving through a pipe 6. The application of the present invention to pipe 6 is for exemplary purposes only, as the components of optical measurement system 2 may be configured to monitor steam quality within any chamber or passageway of a closed vessel which holds steam. To allow passage of radiant energy transversely across the flow of steam 4, a first window 8 and a second window 10 are provided on opposite sides of pipe 6. Windows 8 and 10 may be formed of sapphire or any other material which is suitably transmissive of radiant energy at the desired wavelengths and is capable of withstanding the temperature and pressure exhibited by steam 4. Sapphire is currently preferred due to its resistance to degradation and stress in high pressure environments, enabling the use of relatively thin windows. However, alternative materials such as diamond, for enhanced long-term stability, may be used as well. It is also contemplated that the radiant energy may be of a type or wavelength that may be passed directly through the material of pipe 6, in which case windows will not be required. Of course, a pipe segment may be formed of a suitably transmissive material in lieu of using windows.

In general terms, optical measurement system 2 comprises an emitter 12 associated with first window 8 and a detector 14 associated with the opposing second window 10. Optical measurement system 2 further comprises a power source 16 for supplying power to various transmission components of emitter 12 and detector 14, as well as a controller 18 for the purposes of managing radiant energy transmission and data logging. Controller 18 may comprise, for instance, one or more microprocessors having associated memory and programmed to direct the operation of power source 16 and receive and interpret signal data conveyed from detector 14. As seen if FIG. 1, when driven by power source 16, emitter 12 produces a beam of radiant energy 20 which is directed through first window 8 in pipe 6 and passes across the flow of steam 4. The beam of radiant energy 20 then exits second window 10 in pipe 6, and is collected by detector 14. Detector 14 generates electrical signals 21 in relation to the intensity of the beam of radiant energy 20, which electrical signals 21 are conveyed to controller 18. In this manner, controller 18 may calculate the loss of intensity of the beam of radiant energy 20 due to absorption while passing through the flow of steam 4, and thereby determine steam quality by comparing initial radiant energy beam intensity, or power input corresponding to the initial radiant energy beam intensity (which may be simpler when efficiency of power conversion is known or determinable) to the intensity of the corresponding beam after passage through the steam. As used herein, any reference to employing initial radiant energy beam intensity encompasses using power input to the laser diode or other radiant energy source.

Figure 2:
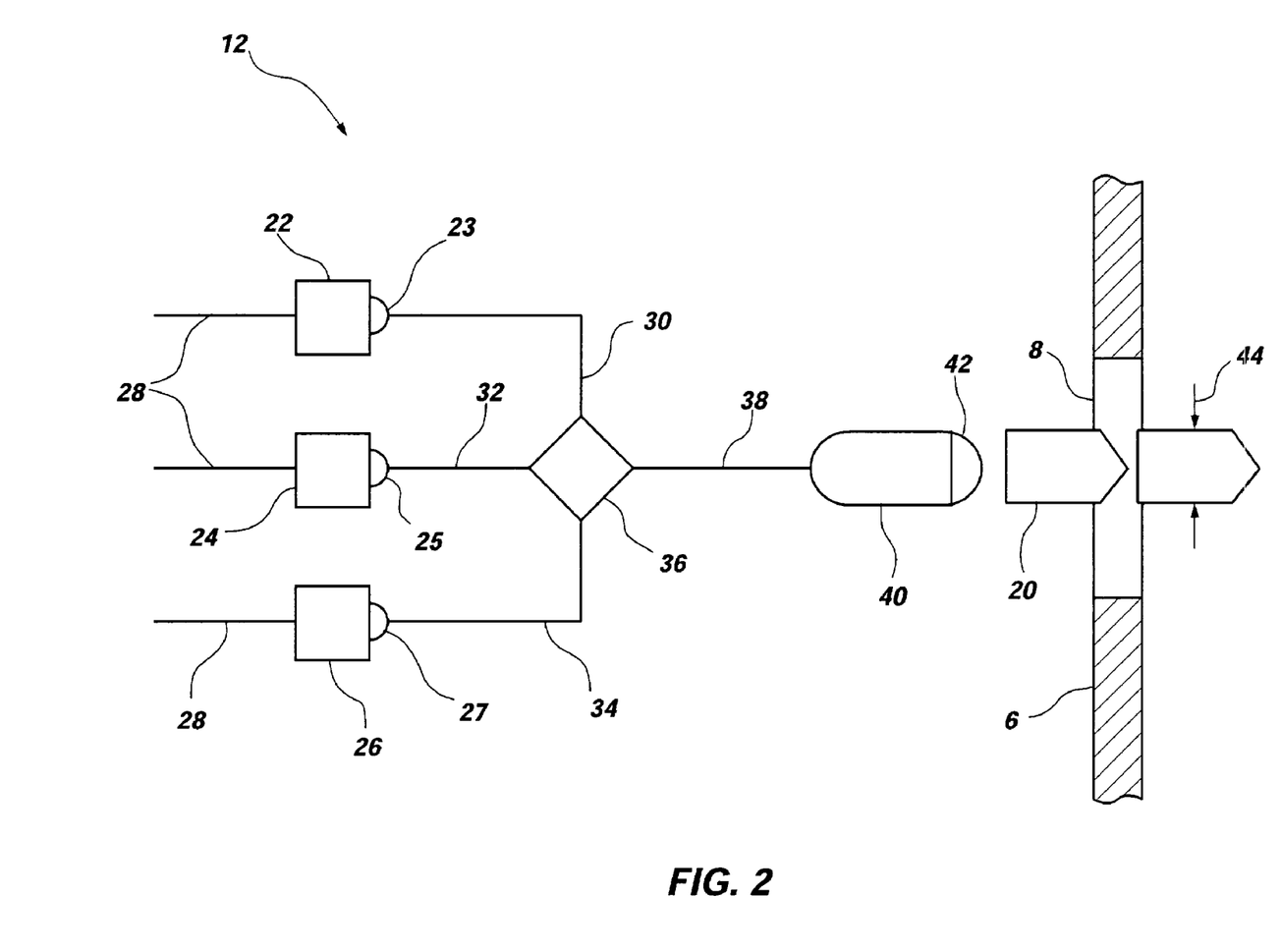
FIG. 2 is a schematic view showing the components of an emitter suitable for use with the optical measurement system depicted in FIG. 1.

FIG. 2 is a schematic view of the operation and function of the components of emitter 12. A key feature of the present invention is the inclusion of three laser diodes 22, 24 and 26, each of which generate an independent radiant energy signal of specific wavelength for subsequent transmission through the flow of steam 4. The first laser diode 22 is configured to generate a radiant energy signal 23 at a wavelength sensitive to absorption by water in the vapor phase. The second laser diode 24 is configured to generate a radiant energy signal 25 at a wavelength sensitive to absorption by water in the liquid phase. The third laser diode 26 generates a radiant energy signal 27 at a wavelength that will pass through water in either the liquid or vapor phases without significant absorption. Example wavelengths exhibiting the desired absorption characteristics are in the range of 980 nm for the first laser diode 22, 1550 nm for the second laser diode 24, and 1060 nm for the third laser diode 26; however, the use of other wavelengths is possible. By using multiple wavelengths having the described varying absorptive properties, the separate effects of the liquid and vapor components of steam 4 may be measured and correlated. Employing a third wavelength also enables compensation for scattering effects, which may affect the accuracy of absorption readings. Accordingly, the present invention provides more accurate and sensitive steam quality measurements than those offered by prior art optical systems.

Power for signal generation is provided by conductive lines 28 communicating with power source 16. Laser diodes 22, 24 and 26 are connected to fiber-optic cables 30, 32 and 34, respectively, for routing of the independent radiant energy signals 23, 25 and 27. Using fiber optics allows laser diodes 22, 24 and 26 to be remotely located from a monitoring site which may be inhospitable in terms of environment or convenience of access. The use of laser diodes in the present invention is therefore desirable due in part to their ability to transmit radiant energy over long pathways without significant divergence of the radiant energy signals. It is feasible, however, that other devices for generating radiant energy at multiple wavelengths may be incorporated for use with the present invention. For example, conventional light-emitting diodes or non-diode type laser or focused conventional light sources may be used in place of laser diodes 22, 24 and 26.

Fiber-optic cables 30, 32 and 34 terminate at a fiber-optic combiner 36 which merges radiant energy signals 23, 25 and 27 into one fiber-optic cable 38 to form the single beam of radiant energy 20. Combination of the multiple wavelengths of radiant energy generated by laser diodes 22, 24 and 26 is accomplished by multiplexing their signals. In one exemplary embodiment, the signal combination may be carried out using frequency domain multiplexing. Under this method, laser diodes 22, 24 and 26 are separately modulated by power source 16 such that the beam of radiant energy 20 contains wavelengths of the radiant energy signals 23, 25 and 27 at different frequencies. In another exemplary embodiment, the signal combination is carried out using wavelength division multiplexing. With wavelength division multiplexing laser diodes 22, 24 and 26 are not separately modulated, but rather are operated concurrently, and the resulting beam of radiant energy 20 carries all three wavelengths of radiant energy signals 23, 25 and 27 at a common frequency. The type of multiplexing determines the manner in which detector 14 collects the beam of radiant energy 20, as described in further detail below.

Referring again to FIG. 2, fiber-optic cable 38 terminates in a collimator 40 positioned outside of the first window 8 in pipe 6 for aligning and transmitting the beam of radiant energy 20 across the flow of steam 4. Collimator 40 is designed to include a graded index lens 42 which expands the beam of radiant energy 20 carried by fiber-optic cable 38 into a relatively large diameter 44. Graded index or "GRIN" lenses rely on differential refractive indexes of material rather than shape for their optical properties, and are known for use with optical communications because of this feature. By expanding the beam of radiant energy 20, it will be passed through a larger cross-section of steam 4 as it is transmitted across pipe 6. This provides a larger data sample and reduces the noise contribution from scattering effects, providing a more accurate measurement. The diameter 44 of the beam of radiant energy 20 might be expanded up to a range of about 6 mm to 80 mm, for example, whereas prior art optical systems typically have beam diameters of about 1 mm. The maximum allowable beam diameter will, of course, be limited by the size of the passageway or other closed vessel where the measurement is to be made. If the diameter of pipe 2 is smaller than the upper limits of the above size range, then a correspondingly smaller diameter beam would be employed in order to pass through the windows. As noted previously, the use of an enlarged diameter laser beam of radiant energy 20 may enable accurate steam quality measurement without the use of a third wavelength due to reduction in significance of scattering effects on the larger beam. Still further, an enlarged diameter laser beam may enable steam quality measurement suitable for some applications using a single wavelength.

Returning to FIG. 1, after the beam of radiant energy 20 passes through the flow of steam 4 within pipe 2 it is collected by detector 14. Detector 14 utilizes a receiver 46 with a graded index lens 48 (FIGS. 3 and 4) positioned outside the second window 10 for collecting the beam of radiant energy 20. The use of graded index lenses 42 and 48 for focusing and transmission of the beam of radiant energy 20 across pipe 6 and receipt thereof reduces the sensitivity to positioning and alignment exhibited by other lens types, making optical measurement system 2 easier to install and maintain. Graded index lenses of the type and size described above are commercially available from vendors such as Lightpath Technologies of Albuquerque, N. Mex.

Figure 3:
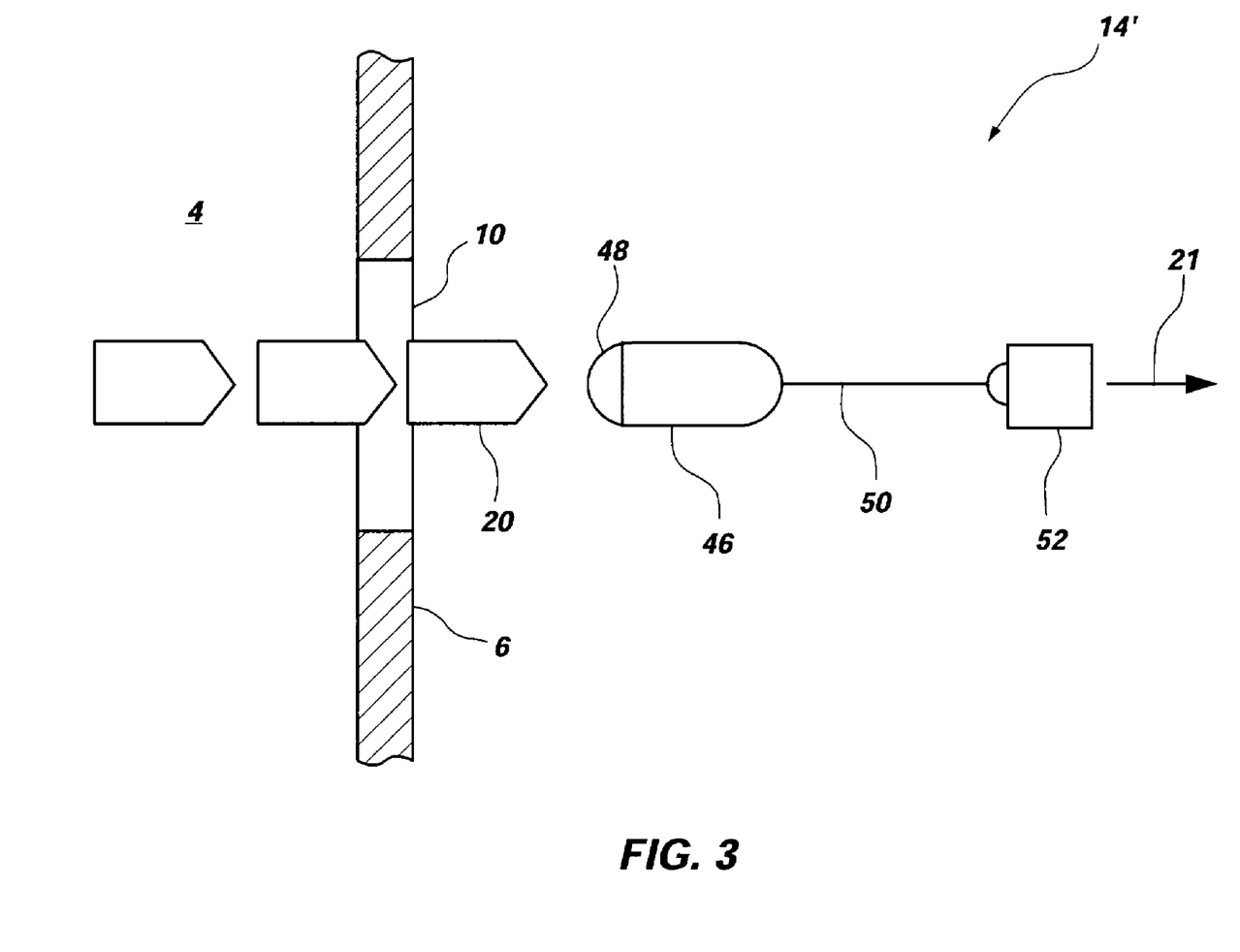
FIG. 3 is a view showing the components of a detector embodiment suitable for use with the optical measurement system depicted in FIG. 1.

FIG. 3 shows a view of the components of a detector 14' used in an exemplary embodiment of the present invention wherein frequency domain multiplexing has been employed (FIG. 1) to combine the radiant energy signals 23, 25 and 27 of laser diodes 22, 24 and 26 into the beam of radiant energy 20. As described above, detector 14' includes a receiver 46 with graded index lens 48 for collecting the beam of radiant energy 20. Graded index lens 48 focuses the beam of radiant energy 20 into a fiber-optic cable 50 connected to receiver 46 for routing. Fiber-optic cable 50 terminates at a photo diode 52 that generates electrical signals 21 corresponding to radiant energy intensity, and conveys them to controller 18 (FIG. 1). Based on the modulation timing of laser diodes 22, 24 and 26 by power source 16, controller 18 then separates electrical signals 21 to provide measurement data in the form of energy losses for the radiant energy signals 23, 25 and 27 and each of the corresponding wavelengths.

Figure 4:
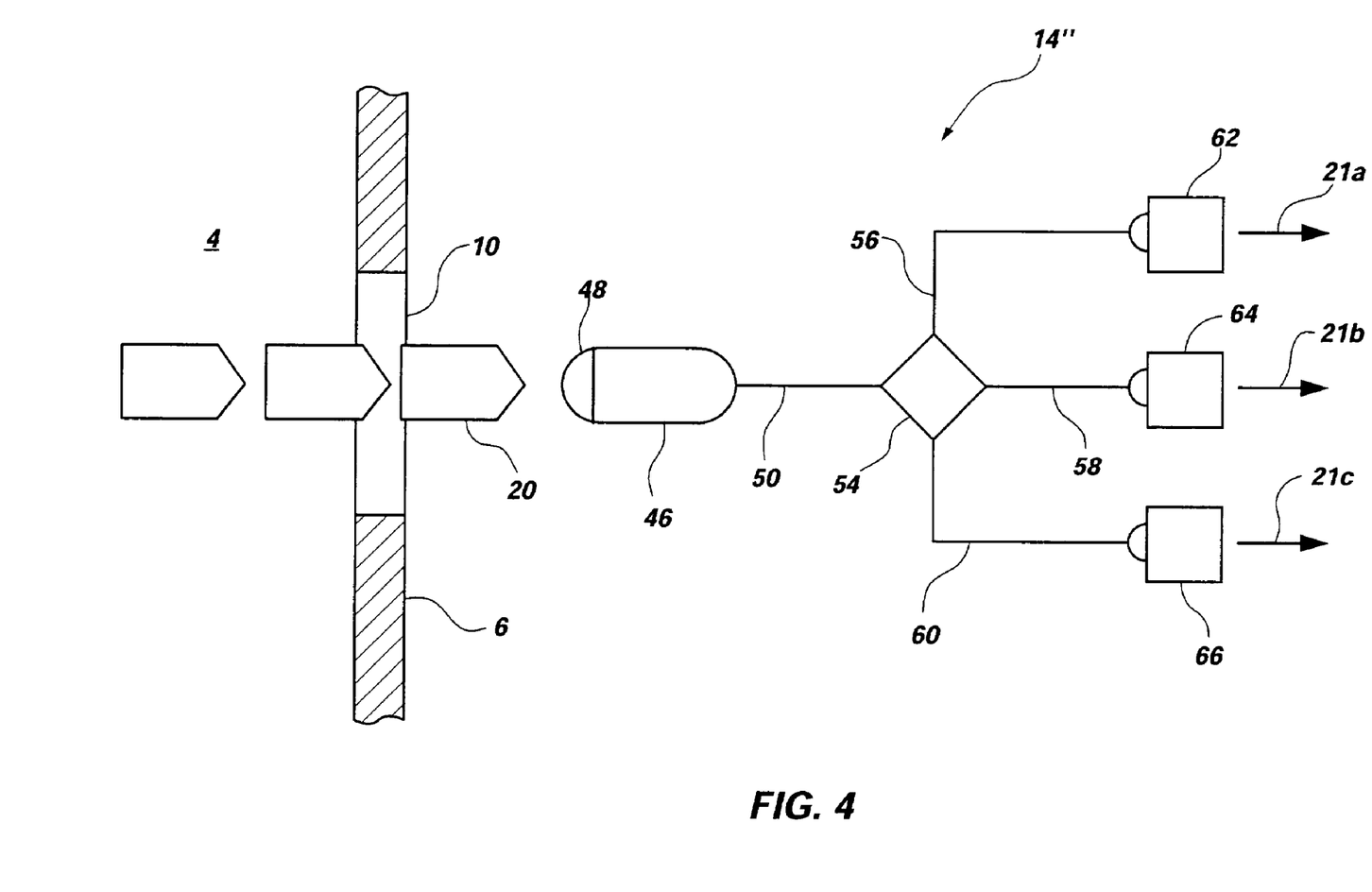
FIG. 4 is a view showing the components of an alternative detector embodiment suitable for use with the optical measurement system depicted in FIG. 1.

FIG. 4 shows a view of the components of a detector 14" in another exemplary embodiment of the present invention wherein a wavelength division multiplexing scheme has been used to combine the radiant energy signals 23, 25 and 27. Detector 14" includes receiver 46, graded index lens 48 and fiber-optic cable 50 which perform the same function as in detector 14'. In detector 14", however, fiber-optic cable 50 terminates at a wave division demultiplexer 54 for dividing the beam of radiant energy 20 into three separate beams, each beam respectively containing a single wavelength of one of the radiant energy signals 23, 25 and 27. Demultiplexing devices of this type are known in the art, and are commonly constructed as fiberoptic splitters containing gratings which separate out the specific wavelengths of radiant energy for passage into separate fibers. Each wavelength of energy signals 23, 25 and 27 is then directed through one of fiber-optic cables 56, 58 and 60 to a first photo diode 62, second photo diode 64 and third photo diode 66, respectively, each photo diode 62, 64 and 66 being sensitive to a specific wavelength relating to one of the radiant energy signals 23, 25 and 27. In this manner, photo diodes 62, 64 and 66 generate individual electric signals 21a, 21b and 21c corresponding to the radiant energy intensity for each of the radiant energy signals 23, 25 and 27 transmitted by laser diodes 22, 24 and 26. Accordingly, controller 18 is provided with separate measurement data indicative of energy losses for each of the associated radiant energy wavelengths.

While the detector embodiments have been described in terms of photo diodes, it is possible that photo detectors such as spectrally filtered photo diodes in the form of charge coupled devices (CCD's) or other monochrometer or spectrometer devices could be used as well. It is also possible that further wavelengths of radiant energy might be added into the beam of radiant energy 20 which are sensitive to specific contamination species possibly contained in steam 4. This would be accomplished, for example, by including additional laser diodes to emit the further wavelengths. Under frequency domain multiplexing, the additional laser diodes would be modulated at supplemental unique frequencies and the modulation timing to would be configured to further separate the frequencies into electrical signals at photo diode 52 to provide measurement data for the contamination species. Under wavelength division multiplexing, wave division demultiplexer 54 would be configured to divide the wavelengths from the additional laser diodes into further separated beams which would then be passed to a corresponding number of additional photo diodes for measurement. With the wavelength division multiplexing scheme, the wave division demultiplexer 54 might be replaced with a conventional fiber optic splitter which does not separate out the wavelengths, but instead sends a portion of beam 20 containing all of the radiant energy wavelengths to photo detector devices formed as a spectrally filtered array.

Under any of the foregoing multiplexing approaches, the measurement data supplied to controller 18 may then be used to determine the amount of energy absorption associated with each wavelength. In the illustrated embodiments, this is accomplished by comparing the intensity of each of radiant energy signals 23, 25 and 27 (or the equivalent power input) when they are transmitted from laser diodes 22, 24 and 26 to their intensity when received at photo diode 52 or photo diodes 62, 64 and 66. Once the amount of absorption is obtained, the steam quality may be determined. For instance, using known constants for the absorption effect of liquid and vapor water on given wavelengths of radiant energy, controller 18 may be programmed to calculate steam quality based on the relationship of absorption to liquid and vapor concentrations under Beer's law. Alternatively, absorption levels recorded by optical measurement system 2 could be matched to standardized values for steam quality under the same conditions using measurement techniques such as calorimetry.

Because amounts of absorption for both the liquid and vapor components of steam 4 are provided in terms of the separate wavelengths of radiant energy generated by laser diodes 22 and 24, they may be correlated with one another to produce a more accurate steam quality measurement. The use of laser diodes further provides high intensity and energy stability for beam transmission, and enables more precise selectivity to specific wavelengths. Because laser generated beams do not substantially diverge during transmission, a consistent beam cross section across the measurement path will be obtained which better models the true nature of the steam cross section penetrated thereby. This makes the present invention suitable for monitoring high-quality steam levels of, for example, 98% to 100% steam quality and particularly 99.5% and above where prior art measurement systems may lack the necessary sensitivity. Furthermore, for lower steam quality levels, scattering of radiant energy due to increased liquid water may influence absorption measurements of conventional optical measurement systems. By using the minimally absorbed wavelength of radiant energy generated by laser diode 26 as a reference point, any scattering effects on the absorption measurements may be recognized and compensated for, thereby enhancing the dynamic response of the system of the present invention and extending the lower end of the range of accuracy thereof.

In summary, the above-described embodiments of the present invention provide an optical steam quality measurement system that offers precision on-line monitoring of steam quality by utilizing a multiple wavelength absorption method for measuring the liquid and vapor components of steam. The system is also well suited for placement within a wide range of environments due to the incorporation of compact and reliable optical semiconductor emitter and detector technology.

Although the present invention has been depicted and described with respect to the illustrated embodiments, various additions, deletions and modifications are contemplated without departing from its scope or essential characteristics. For instance, when measuring steam of high quality where there will be minimal scattering of radiant energy, or when large beam diameters are employed such that noise from scattering effects is negligible, it might be desirable to use only one or two wavelengths of radiant energy to measure absorption. This would reduce the number of required components and simplify the system structure, while still providing the benefits exhibited by laser diode radiant energy transmission. Further, while described in terms of monitoring steam quality based on the presence of liquid water, it may also be configured to monitor for different compositions. This would be beneficial in processes like geothermal energy production wherein steam supplied from subterranean sources may be contaminated with gases and vapors which are harmful to steam turbine components or other equipment. By transmitting a wavelength of radiant energy sensitive to absorption by these harmful gases and vapors, steam flow could be monitored for their occurrence to prevent damage. Another application may involve measuring the content of liquid water in gas flows used for manufacturing semiconductor devices, which processes are highly sensitive to moisture contamination and the resulting semiconductor devices and in-process substrates to moisture damage.

The scope of the invention is, therefore, indicated by the appended claims rather than the forgoing described embodiments. All changes which come within the meaning and range of equivalency of the claims are to be embraced within their scope.

What is claimed is:

1. An apparatus for measuring the quality of steam contained in a closed vessel, comprising:
    an emitter configured and positioned to transmit radiant energy through a volume of steam within the closed vessel, wherein the radiant energy comprises:
        a first wavelength of radiant energy more sensitive to absorption by liquid water than by water vapor;
        a second wavelength of radiant energy more sensitive to absorption by water vapor than by liquid water;
        a third wavelength of radiant energy less sensitive to absorption by liquid water than the first wavelength of radiant energy and less sensitive to absorption by water vapor than the second wavelength of radiant energy;
    a detector configured and positioned to receive the radiant energy transmitted from the emitter after passage through the volume of steam and to generate at least one electrical signal corresponding to an intensity for each of the first, second and third wavelengths of radiant energy received thereby; and
    a controller configured to receive and interpret the quality of steam from a quantitative relationship in the at least one electrical signal of the intensity of each of the first, second and third wavelengths of radiant energy received at the detector.

2. The apparatus according to claim 1, wherein the closed vessel is a steam pipe, and further comprising:
    a first window exposing a flow of steam through a side of the steam pipe, wherein the emitter is oriented to transmit the radiant energy through the first window; and
    a second window exposing the flow of steam through an opposite side of the steam pipe, wherein the detector is oriented to receive the radiant energy through the second window.

3. The apparatus according to claim 1, wherein the emitter comprises:
    a first radiant energy source configured to generate the first wavelength of radiant energy;
    a second radiant energy source configured to generate the second wavelength of radiant energy; and;
    a third radiant energy source configured to generate the third wavelength of radiant energy.

4. The apparatus according to claim 3, wherein the first, second and third energy sources comprise laser diodes.

5. The apparatus according to claim 3, wherein the emitter further comprises:
    a first fiber-optic cable configured to carry the first wavelength of radiant energy from the first radiant energy source to a fiber-optic combiner;
    a second fiber-optic cable configured to carry the second wavelength of radiant energy from the second radiant energy source to the fiber-optic combiner; and
    a third fiber-optic cable configured to carry the third wavelength or radiant energy from the third radiant energy source to the fiber-optic combiner, wherein the fiber-optic combiner is configured to merge the first, second and third wavelengths of radiant energy into a single fiber-optic cable to form a single beam of radiant energy.

6. The apparatus according to claim 5, wherein the emitter further comprises:
    a collimator operably coupled to the single fiber-optic cable and configured to expand a diameter of the single beam of radiant energy.

7. The apparatus according to claim 1, wherein the emitter comprises:
    a collimator configured to transmit the first, second and third wavelengths of radiant energy in a single beam of radiant energy through the volume of steam.

8. The apparatus according to claim 7, wherein the collimator comprises:
    a graded index lens configured to expand a diameter of the single beam of radiant energy.

9. The apparatus according to claim 8, wherein the graded index lens is configured to expand the diameter of the single beam of radiant energy to within a range of about 6 mm to 80 mm.

10. The apparatus according to claim 1, wherein the detector comprises:
    a photo detector configured to detect the first, second and third wavelengths of radiant energy and to generate an electrical signal corresponding to the intensity of each of the first, second and third wavelengths of radiant energy.

11. The apparatus according to claim 10, wherein the detector further comprises:
    a receiver configured to collect the radiant energy transmitted by the emitter; and
    a fiber-optic cable operably coupled to the receiver and configured to carry the radiant energy from the receiver to the photo detector.

12. The apparatus according to claim 11, wherein the receiver comprises:

a graded index lens configured to collect the radiant energy transmitted by the emitter.

13. The apparatus according to claim 10, wherein the photo detector comprises a photo diode.

14. The apparatus according to claim 1, wherein the detector comprises:
- a first photo detector configured to detect the first wavelength of radiant energy;
- a second photo detector configured to detect the second wavelength of radiant energy; and
- a third photo detector configured to detect the third wavelength of radiant energy.

15. The apparatus according to claim 14, wherein the detector further comprises:
- a receiver configured to collect the radiant energy transmitted by the emitter;
- a single fiber-optic cable operably coupled to the receiver and configured to carry the radiant energy therefrom to a wave division demultiplexer;
- a first fiber-optic cable operably coupled to the wave division demultiplexer and configured to carry the radiant energy therefrom to the first photo detector;
- a second fiber-optic cable operably coupled to the wave division demultiplexer and configured to carry the radiant energy therefrom to the second photo detector; and
- a third fiber-optic cable operably coupled to the wave division demultiplexer and configured to carry the radiant energy therefrom to the third photo detector.

16. The apparatus according to claim 15, wherein the receiver comprises:
- a graded index lens configured to collect the radiant energy transmitted by the emitter.

17. The apparatus according to claim 14, wherein the first, second and third photo detectors comprise photo diodes.

18. The apparatus according to claim 1, wherein the emitter is configured to transmit the radiant energy through the steam as a single beam of radiant energy containing the first, second, and third wavelengths of radiant energy, and further comprising
- a power source configured to supply power to the emitter for generating the first, second and third wavelengths of radiant energy.

19. The apparatus according to claim 1, wherein the controller is configured to direct the operation of the power source such that the single beam of radiant energy comprises a transmission having separate frequencies for each of the first, second and third wavelengths of radiant energy.

20. The apparatus according to claim 19, wherein the controller is further configured to generate a measurement of loss of intensity for each of the first, second and third wavelengths of radiant energy after passage through the steam using frequency domain multiplexing and, optionally, to correlate the losses of intensity to steam quality.

21. The apparatus according to claim 18, wherein the controller is configured to direct the operation of the power source such that the single beam of radiant energy comprises a transmission having a single frequency for each of the first, second and third wavelengths of radiant energy.

22. The apparatus according to claim 21, wherein the controller is further configured to generate a measurement of loss of intensity for each of the first, second and third wavelengths of radiant energy after passage through the steam using wavelength division multiplexing and, optionally, to correlate the losses of intensity to steam quality.

23. The apparatus according to claim 1, wherein the first wavelength of radiant energy is about 980 nm, the second wavelength of radiant energy is about 1550 nm and the third wavelength of radiant energy is about 1060 nm.

24. A method for measuring the quality of steam contained in a closed vessel, comprising:
- transmitting a first wavelength of radiant energy more sensitive to absorption by liquid water than by water vapor through the steam;
- transmitting a second wavelength of radiant energy more sensitive to absorption by water vapor than by liquid water through the steam;
- transmitting a third wavelength of radiant energy less sensitive to absorption by liquid water than the first wavelength of radiant energy and less sensitive to absorption by water vapor than the second wavelength of radiant energy through the steam;
- measuring a loss in intensity for each of the first, second and third wavelengths of radiant energy after passage thereof through the steam; and
- correlating the loss of intensity of the first wavelength of radiant energy with the loss of intensity of the second wavelength of radiant energy to provide a measurement of the quality of the steam, the quality of the steam identifying a relationship between a quantity of the liquid water in the steam to a quantity of the water vapor in the steam.

25. The method according to claim 24, wherein the closed vessel is a steam pipe, and further comprising:
- providing a first window for exposing a flow of steam through a side of the steam pipe;
- providing a second window for exposing the flow of steam through an opposite side of the steam pipe; and
- passing the first, second and third wavelengths of radiant energy through the first and second windows for transmission across the flow of steam.

26. The method according to claim 24, further comprising:
- generating the first wavelength of radiant energy with a first radiant energy source;
- generating the second wavelength of radiant energy with a second radiant energy source; and
- generating the third wavelength or radiant energy with a third radiant energy source.

27. The method according to claim 26, wherein the first, second and third radiant energy sources are selected to comprise laser diodes.

28. The method according to claim 26, further comprising:
- merging the first, second and third wavelengths of radiant energy into a single beam of radiant energy for transmission across the flow of steam.

29. The method according to claim 28, further comprising:
- expanding a diameter of the single beam of radiant energy prior to transmission across the flow of steam.

30. The method according to claim 24, further comprising:
- passing the first, second and third wavelengths of radiant energy through a collimator such that the first, second and third wavelengths of radiant energy are transmitted as a single beam of radiant energy through the steam.

31. The method according to claim 30, wherein the collimator comprises a graded index lens, and further comprising:
- expanding a diameter of the single beam of radiant energy with the graded index lens prior to transmission across the flow of steam.

32. The method according to claim 31, wherein expanding the diameter of the single beam of radiant energy comprises expanding the diameter to within a range of about 6 mm to 80 mm.

33. The method according to claim 24, wherein measuring a loss in intensity for each of the first, second and third wavelengths of radiant energy comprises:
   detecting the first, second and third wavelengths of radiant energy with a photo detector; and
   generating an electrical signal indicative of an intensity for each of the first, second and third wavelengths of radiant energy after transmission through the steam.

34. The method according to claim 33, wherein measuring a loss in intensity for each of the first, second and third wavelengths of radiant energy further comprises:
   comparing the intensity for each of the first, second and third wavelengths of radiant energy after transmission through the steam to an intensity for each of the first, second and third wavelengths prior to transmission through the flow of steam to determine a loss in intensity for each of the first, second and third wavelengths of radiant energy.

35. The method according to claim 33, wherein the photo detector is selected to comprise a photo diode.

36. The method according to claim 24, wherein measuring a loss in intensity for each of the first, second and third wavelengths of radiant energy comprises:
   detecting the first wavelength of radiant energy with a first photo detector to generate a first electrical signal indicating an intensity of the first wavelength of radiant energy after transmission through the steam;
   detecting the second wavelength of radiant energy with a second photo detector to generate a second electrical signal indicating an intensity of the second wavelength of radiant energy after transmission through the steam; and
   detecting the third wavelength of radiant energy with a third photo detector to generate a third electrical signal indicating an intensity of the third wavelength of radiant energy after transmission through the steam.

37. The method according to claim 36, wherein measuring a loss in intensity for each of the first, second and third wavelengths or radiant energy further comprises:
   comparing the intensity of the first wavelength of radiant energy after transmission through the steam to an intensity of the first wavelength of radiant energy prior to transmission through the steam to determine a loss in intensity for the first wavelength of radiant energy;
   comparing the intensity of the second wavelength of radiant energy after transmission through the steam to an intensity of the second wavelength of radiant energy prior to transmission through the steam to determine a loss in intensity for the second wavelength of radiant energy; and
   comparing the intensity of the third wavelength of radiant energy after transmission through the steam to an intensity of the third wavelength of radiant energy prior to transmission through the steam to determine a loss in intensity for the third wavelength of radiant energy.

38. The method according to claim 36, wherein the first, second and third photo detectors are selected to comprise photo diodes.

39. The method according to claim 24, further comprising:
   combining the first, second and third wavelengths of radiant energy into a single beam of radiant energy for transmission through the steam using frequency domain multiplexing.

40. The method according to claim 24, further comprising:
   combining the first, second and third wavelengths of radiant energy into a single beam of radiant energy for transmission through the steam using wavelength division multiplexing.

41. The method according to claim 24, wherein measuring a loss in intensity for each of the first, second and third wavelengths of radiant energy further comprises:
   measuring a loss of intensity of the first wavelength of radiant energy due to absorption by the steam;
   measuring a loss of intensity of the second wavelength of radiant energy due to absorption by the steam;
   measuring a loss of intensity of the third wavelength of radiant energy due to scattering by the steam; and
   altering the measurement of the quality of the steam responsive to the loss of intensity of the third wavelength of radiant energy.

42. The method according to claim 24, wherein the first wavelength of radiant energy is selected to be about 980 nm, the second wavelength of radiant energy is selected to be about 1550 nm and the third wavelength of radiant energy is selected to be about 1060 nm.

43. An apparatus for measuring the quality of steam contained in a closed vessel, comprising:
   an emitter configured and positioned to transmit a laser beam of radiant energy of a first and second wavelength through a volume of steam within the closed vessel;
   a detector configured and positioned to receive the laser beam of radiant energy transmitted from the emitter after passage through the volume of steam and to generate at least one electrical signal corresponding to an intensity of the first and second wavelength of radiant energy received thereby; and
   a controller configured to receive and interpret the quality of steam from a quantitative relationship in the at least one electrical signal of the intensity of each of the first and second wavelength of radiant energy received at the detector.

44. The apparatus according to claim 43, wherein the first wavelength of the laser beam of radiant energy is more sensitive to absorption by liquid water than by water vapor.

45. The apparatus according to claim 44, wherein the second wavelength of the laser beam of radiant energy is more sensitive to absorption by water vapor than by liquid water.

46. The apparatus according to claim 45, wherein the laser beam of radiant energy further comprises a third wavelength of radiant energy less sensitive to absorption by liquid water than the first wavelength of radiant energy and less sensitive to absorption by water vapor than the second wavelength of radiant energy.

47. The apparatus according to claim 43, wherein the emitter comprises at least one laser diode configured to generate a laser beam of one of the first and second wavelengths of the laser beam of radiant energy.

48. The apparatus according to claim 47, wherein the emitter further comprises:
   a plurality of laser diodes, each laser diode of the plurality of laser diodes configured to generate a laser beam of a different primary wavelength, each different primary wavelength comprising a wavelength of the first and second wavelengths of radiant energy.

49. The apparatus according to claim 48, wherein the detector is configured to generate an electrical signal corresponding to an intensity of each wavelength of the first and second wavelengths of radiant energy received thereby.

50. The apparatus according to claim 43, wherein the emitter comprises:
a collimator configured to expand a diameter of the laser beam of radiant energy for transmission through the volume of steam.

51. The apparatus according to claim 50, wherein the collimator includes a graded index lens configured to expand the diameter of the laser beam of radiant energy to within a range of about 6 mm to 80 mm.

52. The apparatus according to claim 43, wherein the detector comprises at least one photo diode configured to receive the at least one wavelength of the laser beam of radiant energy.

53. The apparatus according to claim 52, further comprising:
a receiver operably coupled to the at least one photo diode with at least one fiber-optic cable, wherein the receiver includes a graded index lens configured to collect the laser beam of radiant energy.

54. The apparatus according to claim 43, wherein one of the first and second wavelengths of the laser beam of radiant energy comprises a wavelength of radiant energy more sensitive to absorption by at least one specific contamination species contained within the volume of steam than to absorption by liquid water or water vapor.

55. A method for measuring the quality of steam contained in a closed vessel, comprising:
generating a laser beam of radiant energy of a first and second wavelength;
transmitting the laser beam of radiant energy through a volume of steam within the closed vessel;
measuring a loss in intensity for the first and second wavelength of radiant energy after passage thereof through the steam; and
correlating the loss of intensity of the first wavelength of radiant energy with the loss of intensity of the second wavelength of radiant energy to provide a measurement of the quality of the steam, the quality of the steam identifying a relationship between a quantity of the liquid water in the steam to a quantity of the water vapor in the steam.

56. The method according to claim 55, wherein the first wavelength of radiant energy is more sensitive to absorption by liquid water than by water vapor.

57. The method according to claim 56, wherein the second wavelength of radiant energy is more sensitive to absorption by water vapor than by liquid water.

58. The method according to claim 57, wherein generating the laser beam of radiant energy further comprises:
generating a third wavelength of radiant energy less sensitive to absorption by liquid water than the first wavelength of radiant energy and less sensitive to absorption by water vapor than the second wavelength of radiant energy.

59. The method according to claim 55, further comprising:
generating the laser beam of radiant energy of the first and second wavelength with at least one laser diode which generates a laser beam of a primary wavelength.

60. The method according to claim 59, further comprising:
generating the laser beam of radiant energy with a plurality of laser diodes, each laser diode of the plurality of laser diodes generating a laser beam of a different primary wavelength, each different primary wavelength comprising a wavelength of the first and second wavelengths of radiant energy.

61. The method according to claim 60, further comprising:
measuring a loss in intensity for each wavelength of the first and second wavelengths of radiant energy after passage thereof through the steam.

62. The method according to claim 55, further comprising:
expanding a diameter of the laser beam of radiant energy to within a range of about 6 mm to 80 mm prior to transmission across the flow of steam.

63. The method according to claim 62, wherein expanding the diameter of the laser beam of radiant energy comprises expanding the diameter with a graded index lens.

64. The method according to claim 55, wherein measuring a loss in intensity of radiant energy comprises receiving at least one of the first and second wavelength of the laser beam of radiant energy with one photo diode.

65. The method according to claim 55, wherein generating the laser beam of radiant energy comprises generating a wavelength of radiant energy more sensitive to absorption by at least one specific contamination species contained within the volume of steam than to absorption by liquid water or water vapor.

* * * * *